United States Patent [19]
Khanna et al.

[11] Patent Number: 4,798,804
[45] Date of Patent: Jan. 17, 1989

[54] SERUM PRETREATMENT IN DIGOXIN IMMUNOASSAY

[75] Inventors: Pyare Khanna, Fremont; Fred Pearlman, Union City, both of Calif.

[73] Assignee: Syntex (U.S.A.) Inc., Palo Alto, Calif.

[21] Appl. No.: 10,934

[22] Filed: Feb. 5, 1987

[51] Int. Cl.$^4$ .................. G01N 33/00; G01N 1/18; G01N 33/53
[52] U.S. Cl. .................. 436/94; 436/177; 436/518; 436/536; 436/815; 436/825
[58] Field of Search ............... 436/174, 177, 178, 578, 436/536, 815, 825, 94

[56] References Cited

U.S. PATENT DOCUMENTS

| | | | |
|---|---|---|---|
| 4,056,608 | 11/1977 | Ullman et al. | 436/825 |
| 4,121,975 | 10/1978 | Ullman et al. | 436/825 |
| 4,555,504 | 11/1985 | Jones | 536/5 |
| 4,654,311 | 3/1987 | Khanna et al. | 436/825 |
| 4,698,315 | 10/1987 | Farrenkopf et al. | 436/536 |

FOREIGN PATENT DOCUMENTS 0206014 12/1986 European Pat. Off. .

OTHER PUBLICATIONS

Otta et al., *Chem. Abs.*, 97, 187657n, 1982.

Primary Examiner—Robert J. Warden
Assistant Examiner—David A. Saunders
Attorney, Agent, or Firm—Theodore J. Leitereg

[57] ABSTRACT

A method is disclosed for preparing a sample suspected of containing digoxin for determination of digoxin in the sample during an assay. The method comprises contacting the sample with $\beta$-cyclodextrin in an amount and under conditions sufficient to allow a substantial portion of digoxin in the sample to bind to the $\beta$-cyclodextrin. The $\beta$-cyclodextrin with bound digoxin is separated from at least one other component of the medium. Next, the digoxin is released from the $\beta$-cyclodextrin to provide a sample containing digoxin which may be analyzed by any of a number of assay techniques.

20 Claims, No Drawings

SERUM PRETREATMENT IN DIGOXIN IMMUNOASSAY

BACKGROUND OF THE INVENTION

1. Field of the Invention

Digoxin, and derivatives of digoxin, find wide use in cardiac treatment, frequently as a component of digitalis. Digoxin is highly potent in its activity and has a narrow therapeutic range. In addition, the drug can produce serious side effects, so that monitoring the digoxin level in blood is important for the well-being of the patient.

Since the therapeutic range is from about 0.8 to 2.0 ng/ml, it is necessary not only to measure extremely small amounts of digoxin in serum, but also to be able to distinguish between small differences in concentrations. Depending upon the sensitivity of the assay, the digoxin concentration in serum may be insufficient for detection when diluted into the assay medium. Also, naturally occurring materials in the serum sample may modify the observed signal so as to give false results. It would therefore be desirable to provide for a simple means for pretreatment of a serum sample for a digoxin assay. The pretreatment method should be rapid and efficient and provide an assay sample containing the drug in a concentrated amount free of interfering substances.

2. Description of the Prior Art

A radioimmunoassay for determining the digoxin content of a sample is disclosed in U.S. Pat. No. 3,981,982. An enzyme amplification assay is described in U.S. Pat. No. 3,817,837.

SUMMARY OF THE INVENTION

Samples utilized for the determination of digoxin in an assay are pretreated by contacting the sample with $\beta$-cyclodextrin. The contact is carried out in a medium with an an amount of $\beta$-cyclodextrin and under conditions sufficient to allow a substantial portion of digoxin in the sample to bind to the $\beta$-cyclodextrin. The digoxin-bound $\beta$-cyclodextrin is separated from at least one other component of the medium. Next, the digoxin is released from the $\beta$-cyclodextrin to provide a sample digoxin for conducting an assay. The pretreatment method of the invention finds particular application in conjunction with assays employing enzyme of fluorescent labels.

DESCRIPTION OF THE SPECIFIC EMBODIMENTS

Serum samples for digoxin assays are pretreated to provide a medium containing digoxin substantially free of materials present in the serum sample and in a form useful for a digoxin assay determination. It is believed that the present method allows separation of digoxin from endogenous proteins present in serum samples. Under normal circumstances the digoxin is bound to serum proteins to the extent of about 20 to 30 percent.

The method of the present invention comprises contacting in a medium a serum sample suspected of containing digoxin with $\beta$-cyclodextrin in an amount and under conditions sufficient to allow a substantial portion of digoxin in the sample to bind to the $\beta$-cyclodextrin. Next, the $\beta$-cyclodextrin with digoxin bound thereto is separated from at least one other component of the medium such as, e.g., the sample proteins, and the digoxin is released from the $\beta$-cyclodextrin.

The sample suspected of containing digoxin is usually a serological body circulatory fluid or a fraction thereof, which includes blood serum, blood plasma, whole blood, and the like. The sample is contacted with $\beta$-cyclodextrin in a medium, usually an aqueous medium. The aqueous medium can include other agents that increase the binding between digoxin in the sample and the $\beta$-cyclodextrin. Such other agents include, for example, those that increase the ionic strength of the medium such as salts, e.g., halides of alkali metals, e.g., NaCl, KCl, etc., preferably in a concentration of about 0.5–1.5M, and the like.

The amount of $\beta$-cyclodextrin contacted with the medium containing the digoxin sample is sufficient to allow a substantial portion of digoxin in the sample to bind to the $\beta$-cyclodextrin. The amount of $\beta$-cyclodextrin is about from $10^5$ to $10^{10}$ times the amount of digoxin suspected of being in the sample, preferably about from $10^6$ to $10^9$ times the amount of digoxin suspected of being in the sample. Preferably, the $\beta$-cyclodextrin is in substantial excess over the amount of digoxin suspected of being in the sample.

The conditions for contacting of the sample with the $\beta$-cyclodextrin are chosen to allow a substantial portion of digoxin in the sample to bind to the $\beta$-cyclodextrin. Usually at least 50%, preferably at least 75%, more preferably at least 95% of the digoxin becomes bound to the $\beta$-cyclodextrin. The contact is usually carried out at a temperature of about 10° to 40° C., preferably at ambient temperature. The medium containing the sample and the $\beta$-cyclodextrin can be subjected to further treatment immediately or the medium can be held for a period of time as a matter of convenience. The pH of the medium during the contact of the sample and the $\beta$-cyclodextrin is generally about from 5 to 10, preferably from about 6 to 9. All of the conditions chosen should facilitate binding between the digoxin and $\beta$-cyclodextrin or at least not be detrimental to such binding.

Where the $\beta$-cyclodextrin is in insoluble form, the medium containing the sample can be passed through a column containing insoluble $\beta$-cyclodextrin. Alternatively, the medium containing the sample can be combined with the $\beta$-cyclodextrin and the medium can be agitated during the period of contact. Agitation has particular application where $\beta$-cyclodextrin in insoluble powder form is added to a volume of liquid much greater than that of the powder. Accordingly, the aqueous medium can be stirred, shaken, or the like. The idea is to assure good contact between the liquid medium and the solid $\beta$-cyclodextrin.

$\beta$-cyclodextrin is a cycloamylose having seven amylose (homogeneous cyclic alpha-(1–4) linked D-glucopyranose) units; $\beta$-cyclodextrin is, therefore, a cycloheptamylose. The $\beta$-cyclodextrin can be water soluble or polymeric and is available commercially.

After the sample has been contacted with $\beta$-cyclodextrin in an aqueous medium, the medium can be treated to separate $\beta$-cyclodextrin with digoxin bound thereto from at least one other component of the medium. Any convenient method may be utilized to separate the $\beta$-cyclodextrin with bound digoxin from the solution depending on whether the $\beta$-cyclodextrin is in soluble or insoluble form. For example, the solution can be subjected to filtration directly where the $\beta$-cyclodextrin is insoluble. The filter should have a pore size to retain substantially all of the $\beta$-cyclodextrin with bound digoxin while allowing the medium to pass there-through. If monomeric or soluble β-cyclodextrin is used, the solution should be saturated to permit filtration, and there should be excess insoluble material to permit the soluble and insoluble to exchange. Alternatively, if there is no solid phase the soluble β-cyclodextrin may be precipitated prior to filtration, for example, by cooling or salting out or evaporation. After insolubilized β-cyclodextrin with bound digoxin is separated by filtration from the solution, the filter is usually washed from about 0 to 2 times or more with a water or buffer.

When water soluble β-cyclodextrin is added to the medium, the solution can then be subjected to ultrafiltration to separate proteins from the medium. The ultrafilter membrane will be capable of retaining proteins in the medium while allowing the β-cyclodextrin and digoxin to pass through. It will be appreciated that this approach removes proteins from the sample but does not result in a concentrating of digoxin in the sample.

In an alternative approach for separating digoxin bound β-cyclodextrin from the medium, the medium can be contacted with polymerized cyclodextrin. The amount of polymerized β-cyclodextrin employed depends on the size of the sample and the amount of β-cyclodextrin and the aqueous medium. Generally, the amount of polymerized cyclodextrin employed is about from 1 to 500 mg/ml of medium. With small amounts of polymerized cyclodextrin more mixing and contact are required than with larger amounts. However, larger amounts of polymerized cyclodextrin make washing much more difficult. Consequently, one must balance these two factors in selecting the appropriate amount of polymerized cyclodextrin. Again, the polymerized cyclodextrin can be washed 0 to 2 times or more with water or a buffer.

Following the separation of the β-cyclodextrin with bound digoxin, the β-cyclodextrin is treated to release the digoxin therefrom. Generally, the β-cyclodextrin with bound digoxin is contacted in a medium with a releasing agent that is capable of displacing the digoxin by binding to the β-cyclodextrin.

A preferred releasing agent is selected from compounds of the formula:

Y—R—X wherein R is a saturated or unsaturated six membered ring unsubstituted at positions 2, 3, 5, and 6 and X and Y are independently substituents at the 1 and 4 positions of R and are independently selected from the group comprising hydrogen, hydroxy, carboxy, lower alkyl of from 1 to 5 carbon atoms, lower alkyl of from 1 to 5 carbon atoms substituted with hydroxy, carboxy, amino, and sulfonate, with the proviso that the compound is water soluble. Preferred releasing agents are phenols, for example, p-cresol; cyclohexanols, for example, cyclohexanol; and water soluble substituted benzenes, for example, p-methoxybenzoic acid.

The releasing agent is generally present in an aqueous medium. Usually the aqueous medium contains from about $10^{-6}$ to $10^{-1}$M, preferably about $10^{-4}$ to $10^{-2}$M releasing agent. In general, the amount of releasing agent is sufficient to displace substantially all of the digoxin bound to the β-cyclodextrin. The β-cyclodextrin with bound digoxin is contacted with a releasing agent under conditions sufficient to promote the displacement of substantially all of the digoxin from the β-cyclodextrin and to facilitate binding of the releasing agent to the β-cyclodextrin. The temperature during the contact is usually 0° to 50° C., preferably ambient temperature. The pH of the medium during contact is generally 5 to 10, preferably 6 to 9.

The medium containing the released digoxin can represent a 0.2 to 1000 fold concentration of digoxin in the medium over the original sample and will have at least a 10-fold higher digoxin/sample protein ratio. Preferably, the concentration of digoxin in the medium is at least equal to that in the original sample. Thus, the invention provides for removing sample proteins without diluting, and preferably concentrating, the digoxin in a sample to be assayed. The releasing agent should not interfere with a subsequent assay for the determination of the digoxin.

The present method for obtaining a digoxin sample has application in any assay method for the determination of digoxin in a sample suspected of containing digoxin wherein the sample is combined with reagents for detecting the digoxin. The improvement described in the present invention comprises, prior to conducting the assay method, contacting in a medium the sample with β-cyclodextrin in an amount and under conditions sufficient to allow a substantial portion of digoxin in the sample to bind to the β-cyclodextrin. Next, the β-cyclodextrin with bound digoxin is separated from proteins present in the medium. The β-cyclodextrin is then contacted with a releasing agent to release the digoxin from the β-cyclodextrin.

Samples treated to give digoxin samples in accordance with the present invention may be assayed for digoxin by a number of assayed methodologies. The assays may be heterogeneous or homogeneous. The assays often involve immunological reactions. In one embodiment of a homogeneous assay, an antibody, a labeled analyte, and the sample of interest are combined. The signal arising from the label is modified directly or indirectly, upon the binding of the antibody to the labeled analyte. Both the reaction and the detection of the extent thereof are carried out in a homogeneous solution. Labels which may be employed include, fluorescent dyes, enzymes, bacteriophages, co-enzymes and so forth.

In a heterogeneous assay approach, the reagents are usually in the sample of interest, a specific antibody, and a label that is bound to digoxin. The sample is combined with the labeled digoxin and treated with the specific antibody bound to a support, such as a plate or slide. The support is then serarated from the liquid phase and either the support phase or the liquid phase is examined for the presence of the label as indicated by a detectable signal employing means for producing such signal. The signal is related to the presence of the analyte in the sample. Means for producing a detectable signal include the use of radioactive labels, fluorescers, enzymes, and so forth. Exemplary of hetergeneous immunoassays are the radioimmunoassay, immunofluorescence methods, enzyme-linked immunoassays and the like.

For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817,837; 3,850,578; 3,853,987; 3,867,517; 3,901,654; 3,935,074; 3,984,533; 3,966,345; and 4,098,876, which listing is not intended to be exhaustive.

The invention also includes kits comprising, in a packaged combination, (i) β-cylcodextrin in an amount sufficient to allow a substantial portion of digoxin in the sample to be assayed to bind to the β-cyclodextrin, such as the amounts described above, and (ii) a reagent for releasing the bound digoxin from the β-cyclodextrin in an amount sufficient to cause a substantial portion of the digoxin to be released from the β-cyclodextrin, such as the amount and reagents indicated above. Each of the above reagents can be in an aqueous medium in a suitable container such as a vial made of a suitable material such as glass or plastic. The kit also includes ancillary reagents such as buffers and the like in separate containers and so forth. The above kit may be combined with an assay kit for performing a digoxin assay or it may be separate therefrom.

EXAMPLES

The invention is further demonstrated by the following illustrative examples which are provided by way of illustration and not limitation. Parts and percentages are by weight unless otherwise specified.

EXAMPLE 1

A serum pool was prepared containing 1.0 ng/ml of digoxin. Aliquots (900 μl) of this serum pool were combined with 100 μl of 10 mM β-cyclodextrin. Each of the combinations was subjected to ultrafiltration employing an Amicon ultrafilter membrane YM 10.

The above filtrates, an untreated sample from a serum pool (raw serum), and serum from the pool without added β-cyclodextrin subjected to ultrafiltration as described above were assayed employing Clinical Assays $^{125}$I Radioimmunoassay Digoxin Kits following the manufacturer's suggested procedure. The results are summarized in Table 1.

TABLE 1

| Sample | RIA (cpm*) |
| --- | --- |
| Serum + β-CD** | 12680 |
| Raw serum | 13228 |
| Filtered serum | 16041 |
| Serum based Calibrators (ng digoxin/ml) | |
| 0 | 19081 |
| 0.5 | 16444 |
| 1.0 | 13197 |
| 2.0 | 9649 |
| 4.0 | 6276 |

*cpm = counts per minute
**β-CD = β-cyclodextrin

Results show that the β-CD treated sample has slightly more available digoxin than the raw serum and that about half of the digoxin is bound to protein in the absence of β-CD. Thus, without added β-CD the assay sensitivity would be halved by filtering out the protein which can act as an interferent in many assays.

EXAMPLE 2

The procedure of Example 1 was followed. Solutions of β-cyclodextrin (Sigma C-4767, M.W. 1135) in water were prepared at 10, 9, 8.5, 8, 7.5, 7, 6, 4, and 2 mM. Aliquots of serum (900 μl) at 1.0 ng/ml were combined with 100 μl of one of the above solutions of β-cyclodextrin. Assays were conducted as in Example 1. The results are summarized in Table 2.

TABLE 2

| Sample | | RIA (cpm) |
| --- | --- | --- |
| (A) Serum + 10 mM β-CD | | 11080 |
| 8 | | 11356 |
| 6 | | 11334 |
| 4 | | 12387 |
| 2 | | 12903 |
| Raw serum | | 11119 |
| Filtered serum | | 14223 |
| Calibrators (ng digoxin/ml) | | |
| 0 | | 16762 |
| 0.5 | | 14039 |
| 1.0 | | 11439 |
| 2.0 | | 8099 |
| (B) Serum + 9 mM β-CD | | 10943 |
| 8 | | 11512 |
| 7 | | 12005 |
| 6 | | 11786 |
| Raw serum | | 11548 |
| Calibrators (ng digoxin/ml) | | |
| 0 | | 16847 |
| 0.5 | | 13950 |
| 1.0 | | 11422 |
| 2.0 | | 8358 |
| (C) Serum + 8.5 mM β-CD | | 10548 |
| 8.0 | | 10906 |
| 7.5 | | 11098 |
| 7.0 | | 11026 |
| Raw serum | | 10967 |
| Calibrators (ng digoxin/ml) | | |
| 0 | | 16770 |
| 0.5 | | 13733 |
| 1.0 | | 11154 |
| 2.0 | | 7962 |

EXAMPLE 3

Comparison of EMIT ® Assay and Clinical Assays $^{125}$I Radioimmunoassay on Serum Samples Treated with β-Cyclodextrin and Subsequently with Cycohexanol Patient serum samples positive for digoxin were obtained; 900 μl aliquots from each, or 900 μl of calibrators, were pipetted separately into 12×75 mm test tubes together with 100 μl of 7 mM β-cyclodextrin. The mixtures were centrifuged at about 4000 RPM for 1 hr. after placing in an Amicon ultrafilter membrane YM 10.

Cyclohexanol (5 μl aliquots) was pipetted into 12×75 mm test tubes to which was added 600 μl of ultrafiltrate (serum sample or calibrator) from above. The mixtures were vortexed.

Reagent A: 3.31 g NAD (4.5 mm/test), 1.41 g G-6-phosphate (5.0 mm/test), 0.5 g rabbit serum albumin, RSA, (1%/test) were dissolved in 50 ml volumetric with Basic Buffer at pH 5 (0.55M tris HCl Buffer prepared by dissolving 6.66 g Trizma Base, 0.05% sodium azide (0.5 g), and 0.005% Thimerasol (0.05 g) in 950 ml of deionized water, adjusted to pH 8.1 using con HCl, placed in 1 L volumetric flask, qs to mark with deionized water aliquot adjusted to pH 5 with HCl). To 10 ml of above was added 4.8 μl of polyclonal antibody for digoxin (0.024 μl/test).

Reagent B: 1:83 dilution of digoxin-G-6-phosphate dehydrogenase conjugate prepared as described in U.S. Pat. No. 4,039,385, the disclosure of which is incorporated herein by reference, (120 μl/10 ml) in Enzyme Diluent (pH 6.2) (1% RSA, 0.9% sodium chloride dissolved in Basic Buffer and adjusted to pH 6.2 with HCl).

(A) Each of the above samples and calibrators were assayed in duplicate on the Syva Autocarousel ™ instrument using an EMIT ® assay protocol as follows:
Combine
250 μl sample
200 μl 0.0775M Tris, pH 8.1 with 2 μl of Test Trans- 100 µl of Reagent A
200 µl 0.0775M Tris, pH 8.1
100 µl Reagent B
200 µl 0.0775M Tris, pH 8.1
37° C., 500 nm, 40 sec delay, 90 sec read using a Gilford Stassar III spectrophotometer. Standard deviation and C.V.% were calculated for each.

(B) Each of the samples and calibrators was assayed using the Clinical Assays $^{125}$I Radioimmunoassay according to the manufacturer's suggested protocol.

The results of the above experiments A and B were plotted against each other and are summarized as follows:
Slope 0.955
Intercept −0.047
Corr: 0.882
S.E.E. 0.37
N: 20

It is evident from the above results in Examples 1-3 that the subject method can enhance the accuracy and reproducability of digoxin assays, particularly involving serological fluids. Thus, the present pretreatment allows for a sensitive and efficient method for digoxin assays that results in accurate determinations of digoxin.

Although the foregoing invention has been described in some detail by way of illustration and example for purposes of clarity of understanding, it will be obvious that certain changes and modifications may be practiced within the scope of appended claims.

What is claimed is:

1. A method for preparing a sample suspected of containing digoxin for determination of digoxin in said sample in an assay, which method comprises:
   (a) contacting in a medium a sample with β-cyclodextrin in an amount and under conditions sufficient to allow a substantial portion of digoxin in said sample to bind to said β-cyclodextrin,
   (b) separating β-cyclodextrin with digoxin bound thereto from at least one other component of the medium, and
   (c) releasing said digoxin from said β-cyclodextrin.

2. The method of claim 1 wherein said sample is whole blood.

3. The method of claim 1 wherein said sample is blood serum.

4. The method of claim 1 wherein said β-cyclodextrin is in substantial excess over the amount of digoxin suspected of being in said sample.

5. The method of claim 1 wherein the amount of said β-cyclodextrin is about from $10^6$ to $10^9$ times the amount of digoxin suspected of being in said sample.

6. The method of claim 1 wherein the β-cyclodextrin is water soluble.

7. The method of claim 1 wherein the β-cyclodextrin is polymeric.

8. The method of claim 1 wherein said sample is contacted with said β-cyclodextrin for a period of from about 0.5 to 5 minutes.

9. The method of claim 1 wherein digoxin bound to said β-cyclodextrin is separated from the solution by filtration.

10. The method of claim 1 wherein digoxin bound to said β-cyclodextrin is separated from the solution.

11. The method of claim 1 wherein said digoxin is released from said β-cyclodextrin by contacting digoxin bound to said β-cyclodextrin with a releasing agent that is capable of displacing said digoxin by binding to said β-cyclodextrin.

12. The method of claim 11 wherein said releasing agent is a compound of the formula:

$$Y-R-X$$

wherein
R is a saturated or unsaturated six-membered ring unsubstituted at positions 2, 3, 5 and 6 and
X and Y are independently substituents at the 1 and 4 positions of R and are independently selected from the group consisting of hydrogen, hydroxy, carboxy, lower alkyl of from 1 to 5 carbon atoms, and lower alkyl of from 1 to 5 carbon atoms substituted with hydroxy, carboxy, amino, and/or sulfonate, with the proviso that said compound is water soluble.

13. The method of claim 12 wherein said releasing agent is selected from the group consisting of phenols, cyclohexanols and water soluble 1,4-substituted benzenes.

14. In an assay method for the determination of digoxin in a sample suspected of containing digoxin wherein said sample is combined with reagents for detecting said digoxin, the improvement which comprises:
   (a) prior to conducting said assay method contacting in a medium a sample with β-cyclodextrin in an amount and under conditions sufficient to allow a substantial portion of digoxin in said sample to bind to said β-cyclodextrin,
   (b) separating β-cyclodextrin with digoxin bound thereto from at least one other component of the medium, and
   (c) releasing said digoxin from said β-cyclodextrin.

15. The method of claim 14 wherein said β-cyclodextrin is in substantial excess of the amount of digoxin suspected of being in the sample.

16. The method of claim 14 wherein the β-cyclodextrin is water soluble.

17. The method of claim 14 wherein the β-cyclodextrin is polymeric.

18. The method of claim 14 wherein β-cyclodextrin with digoxin bound thereto is separated from the medium by filtration.

19. The method of claim 14 wherein said digoxin is released from said β-cyclodextrin by contacting said cyclodextrin with digoxin bound thereto with a releasing agent capable of displacing said digoxin and binding to said β-cyclodextrin.

20. A method for preparing a sample suspected of containing digoxin for an assay method to determine digoxin in said sample, which method comprises:
   (a) contacting in an aqueous medium a sample with an amount of soluble or polymeric β-cyclodextrin in substantial excess over the amount of digoxin suspected of being in said sample,
   (b) filtering said medium to separate therefrom β-cyclodextrin with digoxin bound thereto, and
   (c) treating said β-cyclodextrin with an agent selected from compounds of the formula:

$$Y'-R-X'$$

wherein
R is a saturated or unsaturated six-membered ring unsubstituted at positions 2, 3, 5 and 6 and
Y' and X' are independently substituents at the 1 and 4 positions of R and are independently selected from the group consisting of hydrogen, hydroxy, carboxy, and lower alkyl of from 1 to 5 carbon atoms, with the proviso that said compound is water soluble.

* * * * *